United States Patent [19]

Kotani et al.

[11] Patent Number: 5,179,016

[45] Date of Patent: Jan. 12, 1993

[54] RESTRICTION ENZYME SSE 8387I

[75] Inventors: Hirokazu Kotani, Muko; Fusao Kimizuka, Ohmihachiman; Ikunoshin Kato, Uji, all of Japan

[73] Assignee: Takara Shuzo Co., Ltd., Kyoto, Japan

[21] Appl. No.: 698,780

[22] Filed: May 13, 1991

[30] Foreign Application Priority Data

Jun. 25, 1990 [JP] Japan ................... 2-166164

[51] Int. Cl.$^5$ ............................................. C12N 9/22
[52] U.S. Cl. ....................................... 435/199; 435/886
[58] Field of Search .............................. 435/199, 253.5

[56] References Cited

PUBLICATIONS

Kessler, C. et al. (1990) Gene 92, 655–59.
Kotani et al. (1990) Nac. Acids Res. 18(19), 5637–5640.
Nucleic Acids Research vol. 12, No. 11, Jun. 11, 1984, 4507–4516.

Primary Examiner—Charles L. Patterson, Jr.
Attorney, Agent, or Firm—Wenderoth, Lind & Ponack

[57] ABSTRACT

The class II restriction endonuclease Sse 8387I is obtained from Streptomyces Sp 837 (FERM BP-3028). It recognizes the nucleotide sequence 5'-CCTGCA ↓ GG-3' and cleaves at the position indicated by the arrow.

9 Claims, No Drawings

RESTRICTION ENZYME SSE 8387I

This invention relates to a Class-II restriction enzyme which recognizes a specific sequence of eight bases in a double-stranded deoxyribonucleic acid (DNA) molecule and cleaves said DNA molecule at specific sites.

Restriction enzymes are endonucleases that are capable of recognizing a specific sequence of bases in a DNA molecule and cleaving the DNA strands at specific sites. Many kinds of restriction enzymes have so far been found. As a result of the progress in molecular genetics and biochemistry, DNA was proven to be the carrier of genetic information, and since then restriction enzymes have been extensively used for various purposes, such as in the clarification of genetic diseases and in gene manipulation. Recently, attention has been focused on the analysis of giant DNAs, such as chromosome DNAs, thus exalting the importance of restriction enzymes. However, most of the restriction enzymes yet known recognize a sequence of four to six bases, and hence the number of cleavage sites is too great when manipulating a giant DNA, making its analysis difficult in many cases. Thus, there has been a demand for restriction enzymes with less cleavage sites (those capable of recognizing a sequence of eight or more bases) in order to analyze giant DNAs, but only the following three restriction enzymes are known at present as being of this type,

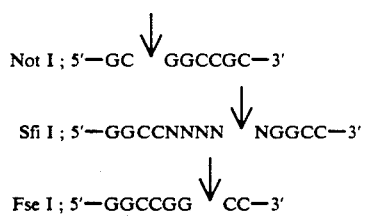

(SEQ ID NO. 1)

wherein G denotes guanine, C stands for cytosine, and N represents G, C, thymine (T) or adenine (A).

Any of the above three restriction enzymes is of the GC-recognition type, thus involving the problem that, especially when manipulating DNAs isolated from mammals in which C in the 5'—C G—3' sequence is methylated in many cases, cleavage does not take place with all of the recognized sequences.

The object of this invention is to provide a restriction enzyme useful in genetic engineering, which is capable of recognizing and cleaving a sequence of eight bases and a nucleotide sequence not having 5'—C G—3' in its vicinity.

In summary, one aspect of this invention relates to a restriction enzyme capable of specifically recognizing the following nucleotide sequence in a DNA molecule and specifically cleaving the same.

```
5'—CCTGCAGG—3'
3'—GGACGTCC—5'
```

The second aspect of this invention relates to the reagents to be used in the genetic engineering method containing the restriction enzyme described above. The third aspect of this invention relates to a process for producing the above restriction enzyme, which comprises growing a microorganism belonging to the genus Streptomyces which is capable of producing the above enzyme and recovering the enzyme thus formed from the culture broth. The fourth aspect of this invention relates to a microorganism belonging to the genus Streptomyces which is capable of producing the above restriction enzyme.

The Class-II restriction enzyme of this invention may be any enzyme that is capable of specifically recognizing and cleaving the above-mentioned base sequence, which enzyme can be obtained by cultivating a strain capable of producing the same, a mutant of the above strain, or a recombinant prepared by isolating the gene coding for the production of said enzyme and transforming it into a different kind of host organism by utilizing ordinary genetic manipulation techniques.

The actual strain producing the restriction endonuclease that recognizes the octanucleotide sequence described above is Streptomyces sp 8387.

This strain was obtained by the present inventors from a soil sample. Its mycological properties are as follows.

(1) Morphological Characteristics

Long aerial mycelia are well-developed and branched. Cutting of mycelia is not observed. Spores are formed well in oatmeal agar and yeast-malt agar. Under a microscope, aerial mycelia do not form whirls, but branch simply. Aerial mycelia form straight or hook-shaped terminals. There are 30–50 spores in a chain or series, and their surfaces are smooth. The spores are column-shaped or elongated spheres, sized 0.8–0.9×1.5–2.0 μm. Sporangia, mobile spores, and sclerotia are not present.

(2) Properties on Various Culture Media

This strain was cultured on various media at 27° C. for 14 days. The results of observation are shown in Table 1.

(3) Physiological Properties (a) Temperature range for growth (yeast-malt agar): 10°–37° C. (optimum temperature for growth: 25°–30° C.)
(b) Liquefaction of gelatin: negative
(c) Hydrolysis of starch: positive
(d) Peptonization of milk: negative; Coagulation of milk: negative
(e) Production of melanoid pigments: negative

TABLE 1

| Medium | Growth | Color of substrate mycelia | Aerial mycelia Formation | Color | Soluble pigments |
|---|---|---|---|---|---|
| Sucrose-nitrate agar | Poor | Pale brown | Poor | Gray | None |
| Glucose-asparagine agar | Good | Creamy yellow | Moderate | Gray | None |
| Glycerol-asparagine agar | Good | Pale brown | Abundant | White | None |
| Starch-inorganic | Moderate | Creamy yellow | Abundant | White | None |

TABLE 1-continued

| Medium | Growth | Color of substrate mycelia | Aerial mycelia Formation | Aerial mycelia Color | Soluble pigments |
|---|---|---|---|---|---|
| salt agar | | | | | |
| Tyrosine agar | Poor | Brown | Abundant | Gray | None |
| Nutritive agar | Moderate | Cream yellow | Poor | Gray | None |
| Yeast-malt agar | Moderate | Brown to pale orange | Moderate | Gray | None |
| Oatmeal agar | Moderate | Creamy yellow | Moderate | Gray | None |
| Peptone-yeast-iron agar | Poor | Pale orange | None | — | None |

(4) Utilization of carbon sources (cultured on Pridham and Gottlieb agar medium at 27° C. for 14 days)

(a) D-Fructose, D-glucose, raffinose, galactose, and mannose are utilized, but i-inositol is not utilized.

(b) Sucrose, D-xylose, and rhamnose are not utilized.

Judging from these properties, it has been determined that this strain belongs to Streptomyces. It produces aerial myclia that are white to gray; the terminals of the aerial mycelia are straight or hook-shaped, and the spore surface is smooth. Substrate mycelia are white to pale brown; melanin is negative.

The present strain was named Streptomyces sp 8387 by the present inventors. The said strain has been deposited at the Fermentation Research Institute, Agency of Industrial Science and Technology, Japan, under FERM BP-3028.

The restriction enzyme recognizing the octanucleotide sequence and produced by Streptomyces sp 8387 strain is named Sse 8387I, recognizes the following nucleotide sequence and cleaves it at the arrow-marked sites.

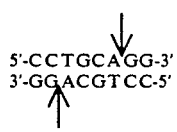

5'-CCTGCAGG-3'
3'-GGACGTCC-5'

Detailed below is the process for producing restriction enzyme Sse 8387I. Any nutrients which the strain used assimilates to produce Sse 8387I may be added to the culture medium. Glucose, maltose, glycerol and others may be used as carbon source, while yeast extract, peptone, corn steep liquor, bouillon and others are suitable as nitrogen source. In addition, minerals and metal salts, such as phosphates, potassium salts and magnesium salts, may also be added.

The yield of Sse 8387I varies depending on culture conditions. Good results are generally obtained at a temperature in the range from 20° to 35° C. and at a pH in the range from 6 to 8; and the highest output is achieved by culture with aeration and agitation for one to three days. It is needless to say that optimal culture conditions should be selected case by case according to the strain used and the composition of culture medium.

Restriction enzyme Sse 8387I produced by the process of this invention is chiefly accumulated in the microbial cells. The grown cells can be isolated from the culture broth, for example, by centrifugation. The enzyme formed can be isolated and purified by using known techniques commonly employed for restriction enzymes. For example, the collected microbial cells are dispersed in a buffer solution, and then broken down by ultrasonic treatment to allow extraction of the enzyme. After removal of the cell debris by ultracentrifugation, ammonium sulfate is added to the extract for salting out, the precipitate is separated out and is dissolved in a buffer solution A (containing 20 mM Tris-HCl, 10 mM 2-mercaptoethanol and 5% glycerol; pH 7.5), and the solution is dialyzed against the same buffer solution. The dialyzate is then purified by ion-exchange chromatography, molecular-sieve chromatography or affinity chromatography, thus giving the restriction enzyme of this invention.

The activity of this enzyme was determined according to the method decribed below.

A substrate solution of the composition shown in Table 2 below was prepared.

TABLE 2

| 10 mM | Tris-HCl, pH 8.0 |
|---|---|
| 10 mM | MgCl$_2$ |
| 7 mM | 2-Mercaptoethanol |
| 50 mM | NaCl |
| 1.0 μg | λ-DNA |

This solution (50 μl) was preheated to 37° C., the sample of Sse 8387I to be tested was then added to allow the enzymatic reaction to proceed at that temperature, and the reaction was stopped ten minutes later by addition of 5 μl of a terminator solution (1% SDS, 50% glycerol, and 0.02% Bromophenol Blue). The reaction mixture was applied to a 0.7% agarose slab gel, and electrophoresis was conducted at a constant voltage of 10 v/cm for about one to two hours. The buffer solution used for electrophoresis was 90 mM Trisborate buffer containing 2.5 mM EDTA (pH 8.3 ). DNA bands can be detected by UV irradiation if 0.5 μg/ml ethidium bromide is previously added to the gel. Electrophoresis was regarded as complete when the number and intensity of the bands for DNA fragments no longer changed.

The enzyme activity which ensures complete digestion of 1 μg λ-DNA after one hour's reaction at 37° C. was defined as one unit.

Restriction enzyme Sse 8387I has the physicochemical properties as described below.

(1) Action and Substrate Specificity

This enzyme is capable of recognizing the base sequence in a double-stranded DNA molecule as shown below and cleaving it at the arrow-marked sites.

5'-CCTGCAGG-3'
3'-GGACGTCC-5'

The base sequence recognized by restriction enzyme Sse 8387I was determined as described below.

Restriction enzyme Sse 8387I cleaved λ-DNA at five sites, AD-2 DNA at three sites, and each of pUC18 DNA and M13 mp18 DNA at one site, but failed to cleave SV40, Col EI, pBR322 and φX174 DNAs. These data and the lengths of obtained DNA fragments suggest that Sse 8387I recognizes the following nucleotide sequence in DNA molecules.

5'—C C T G C A G G—3'

Because this sequence involves the sequence of six nucleotide, 5'—C T G C A G—3', an experiment was performed in which λ-DNA, AD-2 DNA, pUC18 DNA and M13 mp18 DNA were each cleaved by Pst I (a restriction enzyme recognizing the above hexanucleotide sequence) and then with Sse 8387I. The result was that no change was observed in the pattern of DNA fragments finally obtained. It was thus concluded that restriction enzyme Sse 8387I is capable of recognizing the base sequence of 5'—C C T G C A G G—3'.

The sites of cleavage by restriction enzyme Sse 8387I was determined by annealing single-stranded M13 mp18 DNA and a primer of 5'—G T T T C C C A G T C A C G A C—3' (SEQ ID NO: 2) with its 5'-terminal base radioactivated by phosphorylation, synthesizing a double-stranded chain by the use of E. coli DNA polymerase I Klenow fragment, cleaving the double-stranded DNA thus obtained by Sse 8387I, and measuring the chain length of fragments thus formed by electrophoresis on a modified polyacrylamide gel. The obtained product was detected as a spot formed by cleavage at the arrow-marked site of

5'—CCTGCA↓GG—3', and was also detected as a 4-bp shorter spot by blunting treatment with T4 DNA polymerase. Based on these results, the enzyme of this invention was decided to recognize the following base sequence and to cleave it at the arrow-marked sites.

5'-CCTGCA↓GG-3'
3'-GG↑ACGTCC-5'

(2) Optimal conditions for enzymatic activity a) Optimal temperature
The optimal temperature for Sse 8387I was approximately 37° C.
b) Optimal pH
The optimal pH for Sse 8387I was in the range from 7.0 to 9.0.
c) Salt concentration
The optimal salt concentration for Sse 8387I was in the range from 0 to 150 mM in the case of NaCl.
d) MgCl₂ concentration
The enzymatic reaction of Sse 8387I was activated at a MgCl₂ concentration in the range from 5 mM to 20 mM.
e) Molecular weight
The molecular weight of Sse 8387I was 120,000 to 140,000 when measured by the gel filtration method using Sephadex G-200.

The following Example will further illustrate this invention but is not intended to limit its scope.

EXAMPLE 1

Twenty liters of a culture medium having the composition shown in Table 3 below was put in a 30-liter jar fermenter and sterilized by the method commonly employed.

Inoculum (500 ml) of Streptomyces sp 8387 (FERM BP-3028), obtained by shake culture in a medium having the same composition as above at 30° C. for 48 hours, was placed in the above jar fermenter, and cultivation was conducted at 30° C. for 18 hours with aeration (0.5 vvm) and agitation (250 rpm). The grown cells were collected from the culture broth by using a refrigerated centrifuge (about 480 grams of grown cells on wet basis from 20 liters of the culture broth).

TABLE 3

| | |
|---|---|
| Glucose | 10 g |
| Yeast extract | 10 g |
| Polypeptone | 10 g |
| Sodium chloride | 5 g |
| Deionized water | 1 l |
| pH | 7.2 |

Seventy-two grams of the microbial cells obtained above were suspended in 360 ml of buffer solution A, the suspension was treated in a ultrasonic crusher to break down the cell walls, and the resulting mixture was centrifuged (100,000×g, one hour) to remove the residue. To the extract thus obtained (400 ml), was added 4 g of streptomycin, and the mixture was allowed to stand at 4° C. for one hour and centrifuged (10,000×g, 10 minutes). To the supernatant thus obtained, was added ammonium sulfate to 80% saturation, the precipitate which separated out was collected by centrifugation and dissolved in buffer solution A further containing 0.2M KCl, and the solution was dialyzed overnight against the same buffer solution as above.

The dialyzate was then adsorbed on 100 ml of phosphocellulose (P11; Whatman Co.) packed in a column and previously equilibrated with buffer solution A containing 0.2M KCl. After washing with the same buffer as above, the adsorbed portion was eluted with buffer solutions A containing 0.2M to 1.0M KCl (linear concentration gradient technique). The active fractions thus obtained were mixed together, the combined solution was then adsorbed on 30 ml of hydroxyapatite (Bio-rad Laboratories Ltd.) packed in a column and previously equilibrated with 10 mM potassium phosphate buffer solution. After washing with the same buffer as above, the adsorbed portion was eluted with 10 mM to 500 mM potassium phosphate buffer solution (linear concentration gradient technique).

The active fractions thus obtained were mixed together, the combined solution was analyzed for four hours against buffer solution A, and the dialyzate was once more adsorbed on 30 ml of herparine-Sepharose (Pharmacia Fine Chemicals Inc.) packed in a column and previously equilibrated with buffer solution A. After thoroughly washing with the same buffer as above, the adsorbed portion was eluted with buffer solutions A containing 0.2M to 0.8M KCl (linear concentration gradient technique), affording the standard sample of restriction enzyme Sse 8387I.

This standard sample was free from any nonspecific DNase or phosphatase.

The purification method described above gave 500,000-unit activity from 72 g of wet microbial cells.

As is apparent from the foregoing, this invention provides a novel restriction enzyme capable of recognizing and cleaving a sequence of eight bases in double-stranded DNA molecules. The enzyme of this invention is of great use in the field of genetic engineering, for example, for analysis of long-chain DNA molecules and for other purposes.

---
SEQUENCE LISTING
---

(1) GENERAL INFORMATION:
    (i) APPLICANT: Hirokazu KOTANI et al.
    (ii) TITLE OF INVENTION: New Restriction Enzyme
    (iii) NUMBER OF SEQUENCES: 2
    (iv) CORRESPONDENCE ADDRESS:
        (A) ADDRESSEE: Wenderoth, Lind & Ponack
        (B) STREET: 805 Fifteenth Street, N.W., #700
        (C) CITY: Washington
        (D) STATE: D.C.
        (E) COUNTRY: U.S.A.
        (F) ZIP: 20005
    (v) COMPUTER READABLE FORM:
        (A) MEDIUM TYPE: Diskette, 5.25 inch, 500 Kb
        (B) COMPUTER: IBM Compatible
        (C) OPERATING SYSTEM: MS-DOS
        (D) SOFTWARE: DisplayWrite
    (vi) CURRENT APPLICATION DATA:
        (A) APPLICATION NUMBER: 07/698,780
        (B) FILING DATE: May 13, 1991
        (C) CLASSIFICATION:
    (vii) PRIOR APPLICATION DATA:
        (A) APPLICATION NUMBER:
        (B) FILING DATE:
    (viii) ATTORNEY/AGENT INFORMATION:
        (A) NAME:
        (B) REGISTRATION NUMBER:
        (C) REFERENCE/DOCKET NUMBER:
    (ix) TELECOMMUNICATION INFORMATION:
        (A) TELEPHONE:
        (B) TELEFAX:
        (C) TELEX:
(2) INFORMATION FOR SEQ ID NO:1:
    (i) SEQUENCE CHARACTERISTICS:
        (A) LENGTH: 13 Base Pairs
        (B) TYPE: Nucleic acid
        (C) STRANDEDNESS: both
        (D) TOPOLOGY: both
    (ii) MOLECULE TYPE:
    (iii) HYPOTHETICAL:
    (iv) ANTI-SENSE:
    (v) FRAGMENT TYPE:
    (vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:
    (vii) IMMEDIATE SOURCE:
        (A) LIBRARY:
        (B) CLONE:
    (viii) POSITION IN GENOME:
        (A) CHROMOSOME/SEGMENT:
        (B) MAP POSITION:
        (C) UNITS:
    (ix) FEATURE:
        (A) NAME/KEY:
        (B) LOCATION:
        (C) IDENTIFICATION METHOD:
        (D) OTHER INFORMATION:
    (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES:
    (xi) SEQUENCE DESCRIPTION: SEQ ID NO:1:
GGCCNNNNNG GCC    13
(2) INFORMATION FOR SEQ ID NO:2:
    (i) SEQUENCE CHARACTERISTICS:
        (A) LENGTH: 16 Base Pairs
        (B) TYPE: Nucleic acid
        (C) STRANDEDNESS: single
        (D) TOPOLOGY: linear
    (ii) MOLECULE TYPE:
    (iii) HYPOTHETICAL:
    (iv) ANTI-SENSE:
    (v) FRAGMENT TYPE:
    (vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:
    (vii) IMMEDIATE SOURCE:
        (A) LIBRARY:
        (B) CLONE:
    (viii) POSITION IN GENOME:
        (A) CHROMOSOME/SEGMENT:
        (B) MAP POSITION:
        (C) UNITS:
    (ix) FEATURE:
        (A) NAME/KEY:
        (B) LOCATION:
        (C) IDENTIFICATION METHOD:
        (D) OTHER INFORMATION:
    (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES:
    (xi) SEQUENCE DESCRIPTION: SEQ ID NO:2:
GTTTCCCAGT CACGAC    16

What we claim is:

1. A restriction enzyme capable of specifically recognizing the following nucleotide sequence in double-stranded deoxyribonucleic acid and specifically cleaving said nucleotide sequence at the arrow sites,

wherein A, G, T and C represent adenine, guanine, thymine and cytosine, respectively.

2. A restriction enzyme as defined in claim 1, wherein said restriction enzyme is Sse 8387I having the following physicochemical properties:
    (a) Optimal temperature: approximately 37° C.
    (b) Optimal pH: 7.0 to 9.0
    (c) Molecular weight: 120,000 to 140,000.

3. A process for producing a restriction enzyme as defined in claim 2, which comprises cultivating Streptomyces Sp 8387 (FERM BP-3028), and recovering the restriction enzyme from the culture broth.

* * * * *